United States Patent [19]

Starzewski et al.

[11] Patent Number: 4,537,982
[45] Date of Patent: Aug. 27, 1985

[54] PRODUCTION OF ORGANIC NICKEL COMPOUNDS

[75] Inventors: Karl-Heinz A. O. Starzewski, Frankfurt am Main; Josef Witte, Cologne, both of Fed. Rep. of Germany

[73] Assignee: Bayer Aktiengesellschaft, Leverkusen, Fed. Rep. of Germany

[21] Appl. No.: 516,104

[22] Filed: Jul. 22, 1983

[30] Foreign Application Priority Data

Aug. 3, 1982 [DE] Fed. Rep. of Germany ....... 3228865
May 17, 1983 [DE] Fed. Rep. of Germany ....... 3317825
Jun. 11, 1983 [DE] Fed. Rep. of Germany ....... 3321179

[51] Int. Cl.$^3$ ............................................. C07F 15/04
[52] U.S. Cl. ........................................ 556/22; 556/20; 556/21; 556/23; 556/9; 556/12
[58] Field of Search .................................... 260/439 R

[56] References Cited

U.S. PATENT DOCUMENTS 4,097,509 6/1978 Schmidbaur et al. ...... 260/439 R X
4,144,259 3/1979 Fahey et al. ................... 260/439 R
4,185,028 1/1980 Schmidbaur et al. ...... 260/439 R X
4,241,155 12/1980 Hara et al. ................. 260/439 R X
4,293,502 10/1981 Beach et al. ................... 260/439 R
4,310,716 1/1982 Beach et al. .
4,385,007 5/1983 Shook ........................ 260/439 R X
4,416,825 11/1983 Ostermaier ..................... 260/439 R

*Primary Examiner*—Helen M. S. Sneed
*Attorney, Agent, or Firm*—Connolly and Hutz

[57] ABSTRACT

Nickel-compounds, producible by reaction of Nickel-(O)-compound or a compound convertible thereto in situ with two different compounds corresponding to the following formulae

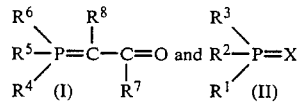

are useful as catalysts in the polymerization of olefins.

6 Claims, No Drawings

PRODUCTION OF ORGANIC NICKEL COMPOUNDS

This invention relates to nickel compounds which are producible by reacting a nickel-(O)-compound or a nickel compound covertible thereto in situ with two different compounds corresponding to the following general formulae:

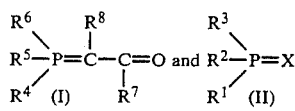

and to the use thereof as catalysts in the polymerisation of olefins.

Transition metal compounds in combination with ylides and the use thereof as catalysts in the polymerisation of olefins are known. Thus U.S. Pat. No. 2,998,416 describes the use of a reaction product of a transition metal compound, such as titanium tetrachloride or nickel chloride, with a compound corresponding to general formula (II) with $X=CR_2$ above. Disadvantages of this known catalyst are: a complicated mixture of numerous components, not stable in storage, difficult to handle, difficult to meter, poor yields, poor activity, poorer activity than in the absence of ylide.

DE-OS No. 2,062,336 describes a reaction product of a nickel-(O)-compound with a compound corresponding to general formula (I) above and/or with an ylide corresponding to the following general formula:

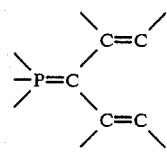

(IV)

as a catalyst for the polymerisation of olefins. Disadvantages of this known catalyst are: no defined compounds, not known whether chemically uniform, no purity criteria, solutions are unstable and yields are unsatisfactory.

In Angew. Chem., 90, 493, (1978), Keim et al. describe a catalyst corresponding to the following formula:

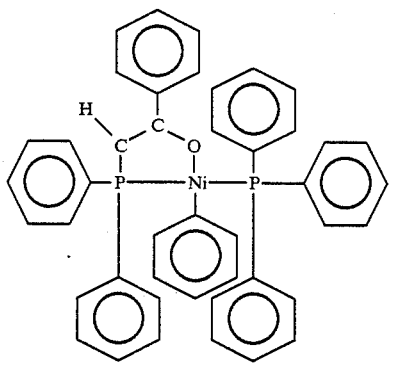

(V)

which unfortunately still shows unsatisfactory activity (max. 6000 moles of ethylene per mole of catalyst) and only gives oligomers.

In addition, EP-OS No. 46 331 describes a nickel catalyst for the polymerisation of olefins which differs from the catalyst according to the present invention in the absence of the X group. Disadvantages of this known catalyst are: sensitivity to temperatures upwards of 50° C. and sensitivity to pressures upwards of about 40 bars.

The nickel catalyst according to DE-OS No. 2,923,206 is also attended by various disadvantages: inadequate activity, relatively high Ni-concentration, and very limited choice of solvents.

There is a need in industry to eliminate the disadvantages in attending conventional nickel catalysts. The advantages afforded by the catalysts according to the present invention are, for example, in part well defined pure substances, obtainable in high yields, quality verifiable by spectroscopy, readily transportable and meterable, stable in storage, thermally stable, relatively stable in air, highly active in highly diluted form and in a number of solvents, highly active over a wide temperature range and highly active over a wide pressure range.

Accordingly, the present invention relates to nickel compounds producible by reacting a nickel-(O)-compound or a nickel compound covertible thereto in situ with two different compounds corresponding to the following general formulae

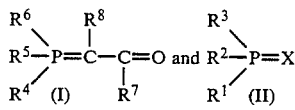

wherein $R^1$, $R^2$ and $R^3$, which may be the same or different, represent optionally by halogen, hydroxy, $C_1$–$C_{20}$-alkoxy or $C_6$–$C_{12}$-aryloxy substituted $C_1$–$C_{20}$-alkyl radicals, $C_6$–$C_{12}$-aryl radicals or $C_3$–$C_8$-cycloalkyl radicals; $C_6$–$C_{12}$-aryl-$C_1$–$C_{20}$-alkyl radicals, $C_1$–$C_{20}$-alkyl-$C_6$–$C_{12}$-aryl radicals, $C_1$–$C_{20}$-alkyl-$C_3$–$C_8$-cycloalkyl radicals, $C_6$–$C_{12}$-aryl-$C_3$–$C_8$-cycloalkyl radicals $C_2$–$C_6$-alkenyl radicals, $C_6$–$C_{12}$-aryl-$C_2$–$C_6$-alkenyl radicals, di-$C_1$–$C_4$-alkylamino radicals and optionally substituted phenoxy and alkoxy radicals X denotes O, $NR^9$ or

$R^4$, $R^5$, $R^6$, $R^7$ and $R^8$, which may be the same or different, represent optionally by halogen, hydroxy, $C_1$–$C_{20}$-alkoxy or $C_6$–$C_{12}$-aryloxy substituted $C_1$–$C_{20}$-alkyl radicals, $C_6$–$C_{12}$-aryl radicals, $C_2$–$C_{30}$-alkenyl radicals or $C_3$–$C_8$-cycloalkyl radicals; $C_6$–$C_{12}$-aryl-$C_1$–$C_{20}$-alkyl radicals, $C_1$–$C_{20}$ alkyl-$C_6$–$C_{12}$-aryl radicals, halogen, hydroxy, $C_1$–$C_{20}$-alkoxy radicals, or $C_6$–$C_{12}$-aryloxy radicals, in addition to which $R^7$ may represent hydrogen, $R^8$ may represent hydrogen or sulphonate and $R^9$, $R^{10}$ and $R^{11}$, which may be the same or different, represent hydrogen, silyl, halogen, nitrophenyl, cyano or $R^1$.

The following radicals are preferred:

(a) for $R^1$, $R^2$ and $R^3$: $C_1$-$C_6$ alkyl, cyclohexyl, phenyl tolyl, benzyl, di-$C_1$-$C_4$-alkylamino, phenoxy or $C_1$-$C_4$-alkoxy;
(b) for $R^5$, $R^6$, $R^7$ and $R^8$: $C_1$-$C_4$-alkyl, cyclohexyl, phenyl, tolyl, benzyl or vinyl;
(c) for $R^4$: $C_6$-$C_{12}$-aryl;
(d) for $R^7$: additionally hydrogen or $C_1$-$C_4$-alkoxy;
(e) for $R^8$: additionally hydrogen or sulphonate; and
(f) for $R^9$, $R^{10}$ and $R^{11}$: hydrogen, chlorine, cyano, trimethyl silyl, $C_1$-$C_6$-alkyl, phenyl, chlorophenyl, nitrophenyl, and $C_1$-$C_6$-alkyl phenyl, $C_2$-$C_6$-alkenyl, and phenyl-$C_2$-$C_6$-alkenyl.

According to the present knowledge the nickel compounds according to the invention are in agreement with the formula

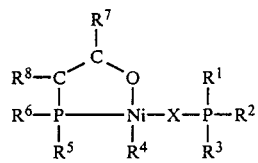

wherein X and $R^1$ to $R^8$ have the above mentioned meaning.

It is preferred to use from 1 to 4 moles of the compound (I) and from 1 to 4 moles of the compound (II) per mole of the nickel-(O) compound and it is particularly preferred to use 1 mole, of the compound (I) and 1 mole, of the compound (II) per mole of the nickel-(O) compound.

The reaction temperature is from 0° to 100° C., more preferably from 20° to 70° C.

The reaction is carried out under anaerobic conditions (for example under an atmosphere of nitrogen or argon) in the presence or absence of a solvent. Any solvents used, such as aromatic solvents, for example benzene or toluene, and aliphatic solvents, for example cyclohexane or hexane, must be inert to the reactants. The reaction is preferably carried out in a solvent.

On completion of the reaction, the catalyst is isolated as a solid, generally by filtration, the solution being concentrated and/or cooled before hand if necessary.

It may even be used directly, i.e. without isolation, for the polymerisation of olefins.

Production of the catalyst may even be carried out in the presence of olefins.

Examples of suitable nickel-(O) compounds ar Ni-(cyclooctadiene)$_2$ and Ni-(allyl)$_2$.

Examples of nickel compounds which may be converted in situ into nickel-(O) compounds are Ni-acetylacetonate and Ni-carboxylates, such as Ni-octanoate and Ni-stearate, which may be reduced using conventional reducing agents, such as boranate, alanate, aluminium alkyls and lithium organyls.

The present invention also relates to the use of the nickel compounds as catalysts in the polymerisation of olefins, particularly ethene.

In the case the compounds according to the invention carry a sulphonate group this can be present in the form of an alkali, ammonium or phosphonium salt. Examples are the sodium, potassium, tetrabutyl ammonium and triphenyldodecyl phosphonium salts.

The compounds of formulae (I) and (II) are known or are prepared according to conventional methods.

The quantity in which the nickel compound is used is not critical. Typical catalyst concentrations are from 10 to $10^{-6}$ moles per liter, preferably from $10^{-2}$ to $10^{-4}$ moles per liter. The quantity of catalyst used, based on ethene, amounts to from 0.005 to 10%, by weight, preferably from 0.01 to 0.1%, by weight.

The following procedures are suitable for the polymerisation of olefins using the catalysts according to the present invention.

(a) initially introducing the solid or dissolved catalyst (or its components), adding the olefin and then heating;
(b) initially introducing the olefin and injecting the catalyst solution or suspension (or its components);
(c) continuously introducing the catalyst solution (or its components) under desired polymerisation conditions (pressure and temperature) established in advance.

Although, therefore, the order in which the components are added is not critical, continuous introduction of the catalyst is preferred from the point of view of process technology.

Examples of suitable solvents or diluents or suspending agents are aliphatic hydrocarbons, such as n-hexane and cyclohexane; aromatic hydrocarbons, such as benzene, toluene and xylene; halogenated hydrocarbons, such as methylene chloride; ketones, such as acetone and methyl ethyl ketone; esters, such as ethyl acetate; acid amides, such as dimethyl formamide; and ethers, such as tetrahydrofuran.

An olefin is a compound which contains a (C=C)-double bond, preferably in the 1-position. Examples of such compounds are ethene, propene and 1-butene. Polymerisation using the catalysts according to the present invention may be carried out both continously and also in batches.

The polymerisation temperature is preferably from 20° to 200° C., more preferably from 60° to 150° C. The olefin pressure should amount to at least 1 bar. The upper limit is not critical. Preferred olefin pressures are from 5 to 1000 bars.

In the case of the ethene polymerisation products with differing molecular weights are obtained in dependence of the ligands of the catalyst.

In addition, the polymerisation solutions contain oligomers (dimers, trimers, etc.).

EXAMPLE 1

2 mMoles of bis-(cyclooctadiene)nickel-(O) in 250 ml of anhydrous, nitrogen-saturated toluene are mixed under nitrogen with 2 mMoles of benzoyl methylene triphenyl phosphorane and 2 mMoles of N-trimethylsilyl triphenyl phosphin-imine. The resulting mixture is then heated from 40° to 60° C. with intensive stirring for about 2 hours. The dark yellow-brown solution is filtrated and used in the following polymerisation of ethene.

By concentration of the solution, addition of hexane and subsequent cooling from 0° to −20° C. yellow crystals are formed.

EXAMPLE 2

General procedure for the nickel ylide-catalysed polymerisation of ethene:

The catalyst according to the present invention, for example in the form of a solution or suspension in toluene, is injected into a prepared autoclave (single pulse injection) or slowly introduced commensurate with the consumption of ethene (multipulse injection). It is possible to use both isolated pure substances (isolated catalysts) and also reaction solutions of the catalyst components ("in situ" catalysts). After a polymerisation time of from 1 to 2 hours, the polymerisation mixture is left to cool, the autoclave is vented and the solid polyethylene is isolated by filtration. The filtrate is analysed by gas chromatography. After removal of the solvent using a rotary evaporator, the quantity of oligomers may be weighed out. Accordingly, the low-boiling fractions are not included in the yields quoted (sum of polymers and oligomers) or in the calculated activity levels (moles of ethene reacted per mole of Ni-catalyst).

The catalysts are prepared according to Example 1 from 2 mMoles of bis-(cyclooctadiene)nickel-(O) and the below mentioned amounts of the components (I) and (II), defined by their substituents X and $R^1$ to $R^9$.

(a) Catalyst: 2 mMoles I ($R^4$, $R^5$, $R^6$=phenyl, $R^8$=H, $R^7$=methyl), 2 mMoles II ($R^1$, $R^2$, $R^3$=phenyl, X=$NR^9$, $R^9$=trimethylsilyl) in 250 ml of toluene (multipulse injection)
Solvent: 1 liter of cyclohexane
Polymerisation pressure: 100 bars ethene
Polymerisation temperature: 100° C.
Total yield: 1281 g (0% of oligomers)
PE melting point: approx. 112° C.
Intrinsic viscosity of PE in tetralin at 140° C: 0.10 dl/g
Catalyst activity: 22875 moles of ethene reacted per mole of nickel.

(b) Catalyst 2 mMoles I ($R^4$, $R^5$, $R^6$=phenyl, $R^8$=H, $R^7$=Methyl), 2 mMoles II ($R^1$, $R^2$, $R^3$=phenyl, X=$NR^9$, $R^9$=trimethylsilyl) in 250 ml of toluene (multipulse injection)
Solvents: 12 liters of cyclohexane
Polymerisation pressure: 10 bars ethene
Polymerisation temperature: 100° C.
Total yield: 1638 g (11% of oligomers)
PE melting point: 116° C.
Intrinsic viscosity of PE in tetralin at 140° C.: 0.09 dl/g
Catalyst activity: 29250 moles of ethene reacted per mole of nickel.

(c) Catalyst 2 mMoles I ($R^4$, $R^5$, $R^6$=phenyl, $R^8$=H, $R^7$=methyl), 2 mMoles II ($R^1$, $R^2$, $R^3$=methyl, X=O) in 250 ml of toluene (multipulse injection)
Solvent: 12 liters of cyclohexane
Polymerisation pressure: 10 bars ethene
Polymerisation temperature: 100° C.
Total yield: 1976 g (7% of oligomers)
PE melting point: 114° C.
Intrinsic viscosity of PE in tetralin at 140° C.: 0.13 dl/g
Catalyst activity: 35286 moles of ethene reacted per mole of nickel.

(d) Catalyst 2 mMoles I ($R^4$, $R^5$, $R^6$=phenyl, $R^8$=H $R^7$=methyl), 2 mMoles II ($R^1$, $R^2$, $R^3$=phenyl, X=O) in 250 ml of toluene (multipulse injection)
Solvent: 12 liters of cyclohexane
Polymerisation pressure: 10 bars ethene
Polymerisation temperature: 100° C.
Total yield: 1268 g (11% of oligomers)
PE melting point: 115° C.
Intrinsic viscosity of PE in tetralin at 140° C.: 0.12 dl/g
Catalyst activity: 22643 moles of ethene reacted per mole of nickel (e) Catalyst 2 mMoles I ($R^4$, $R^5$, $R^6$=phenyl, $R^8$=H, $R^7$=methyl), 2 mMoles II ($R^1$, $R^2$, $R^3$=dimethylamino, X=O) in 250 ml of toluene (multipulse injection)
Solvent: 12 liters of cyclohexane
Polymerisation pressure: 10 bars ethene
Polymerisation temperature: 100° C.
Total yield: 1255 g (14% of oligomers)
PE melting point: 115° C.
Intrinsic viscosity of PE in tetralin at 140° C: 0.13 dl/g
Catalyst activity: 22411 moles of ethene reacted per mole of nickel.

(f) Catalyst 2 mMoles I ($R^4$, $R^5$, $R^6$=phenyl, $R^8$=H, $R^7$=methyl), 2 mMoles II ($R^1$, $R^2$, $R^3$=phenoxy, X=O) in 250 ml of toluene (multipulse injection)
Solvent: 12 liters of cyclohexane
Polymerisation pressure: 10 bars ethene
Polymerisation temperature: 100° C.
Total yield: 1290 g (16% of oligomers)
PE melting point: 118° C.
Intrinsic viscosity of PE in tetralin at 140° C.: 0.13 dl/g
Catalyst activity: 23036 moles of ethene reacted per mole of nickel (g) Catalyst 2 mMoles I ($R^4$, $R^5$, $R^6$, $R^7$=phenyl, $R^8$=H), 2 mMoles II ($R^1$, $R^2$, $R^3$=phenyl, X=$NR^9$, $R^9$=tert.-butyl) in 250 ml of toluene (multipulse injection)
Solvent: 12 liters of cyclohexane
Polymerisation pressure: 10 bars ethene
Polymerisation temperature: 100° C.
Total yield: 1368 g (12% of oligomers)
PE melting point: 118° C.
Intrinsic viscosity of PE in tetralin at 140° C.: 0.11 dl/g
Catalyst activity: 24429 moles of ethene reacted per mole of nickel (h) Catalyst 2 mMoles I ($R^4$, $R^5$, $R^6$, $R^7$=phenyl, $R^8$=H), 2 mMoles II ($R^1$, $R^2$, $R^3$=phenyl, X=$NR^9$, $R^9$=trimethylsilyl), in 250 ml of toluene (multipulse injection)
Solvent: 12 liters of cyclohexane
Polymerisation pressure: 10 bars ethene
Polymerisation temperature: 100° C.
Total yield: 2943 g (2% of oligomers)
PE melting point: 116° C.
Intrinsic viscosity of PE in tetralin at 140° C.: 0.18 dl/g
Catalyst activity: 52554 moles of ethene reacted per mole of nickel.

(i) Catalyst 2 mMoles I ($R^4$, $R^5$, $R^6$, $R^7$=phenyl, $R^8$=H), 2 mMoles II ($R^1$, $R^2$, $R^3$=methyl, X=O) in 250 ml of toluene (multipulse injection)
Solvent: 12 liters of cyclohexane
Polymerisation pressure: 10 bars ethene
Polymerisation temperature: 100° C.
Total yield: 2779 g (6% of oligomers)
PE melting point: 118° C.
Intrinsic viscosity of PE in tetralin at 140° C.: 0.19 dl/g
Catalyst activity: 49625 moles of ethene reacted per mole of nickel.

(j) Catalyst 2 mMoles I ($R^4$, $R^5$, $R^6$, $R^7$=phenyl, $R^8$=H), 2 mMoles II ($R^1$, $R^2$, $R^3$=phenyl, X=O) in 250 ml of toluene (multipulse injection)
Solvent: 12 liters of cyclohexane
Polymerisation pressure: 10 bars ethene
Polymerisation temperature: 100° C.
Total yield: 1849 g (7% of oligomers)

PE melting point: 118° C.
Intrinsic viscosity of PE in tetralin at 140° C.: 0.15 dl/g
Catalyst activity: 33018 moles of ethene reacted per mole of nickel.

(k) Catalyst 2 mMoles I ($R^4$, $R^5$, $R^6$, $R^7$=phenyl, $R^8$=H), 2 mMoles II ($R^1$, $R^2$, $R^3$=dimethylamino, X=O) in 250 ml of toluene (multipulse injection)
Solvent: 12 liters of cyclohexane
Polymerisation pressure: 10 bars ethene
Polymerisation temperature: 100° C.
Total yield: 1842 g (9% of oligomers)
PE melting point: 117° C.
Intrinsic viscosity of PE in tetralin at 140° C.: 0.12 dl/g
Catalyst activity: 32893 moles of ethene reacted per mole of nickel (l) Catalyst 2 mMoles I ($R^4$, $R^5$, $R^6$, $R^7$=phenyl, $R^8$=H), 2 mMoles II ($R^1$, $R^2$, $R^3$=phenoxy), X=O) in 250 ml of toluene (multipulse injection)
Solvent: 12 liters of cyclohexane,
Polymerisation pressure: 10 bars ethene
Polymerisation temperature: 100° C.
Total yield: 2353 g (8% of oligomers)
PE melting point: 115° C.
Intrinsic viscosity of PE in tetralin at 140° C.: 0.15 dl/g
Catalyst activity: 42018 moles of ethene reacted per mole of nickel.

(m) Catalyst 2 mMoles I ($R^4$, $R^5$, $R^6$=phenyl, $R^8$=H, $R^7$=methyl), 2 mMoles II ($R^1$, $R^2$, $R^3$=phenyl, X=$NR^9$, $R^9$=tert.-butyl) in 250 ml of toluene (multipulse injection)
Solvent: 1 liter of cyclohexane
Polymerisation pressure: 100 bars ethene
Polymerisation temperature: 100° C.
Total yield: 1262 g (0% of oligomers)
PE melting point: 111° C.
Intrinsic viscosity of PE in tetralin at 140° C.: 0.10 dl/g
Catalyst activity: 22536 moles of ethene reacted per mole of nickel.

(n) Catalyst 2 mMoles I ($R^4$, $R^5$, $R^6$, $R^7$=phenyl, $R^8$=$SO_3Na$), 2 mMoles II ($R^1$, $R^2$, $R^3$=phenyl, X=O in 230 ml of toluene and 20 ml of dimethylformamide (multipulse injection)
Solvent: 12 liters of cyclohexane
Polymerisation pressure: 10 bars ethene
Polymerisation temperature: 100° C.
Total yield: 680 g (7% of oligomers)
PE melting point: 127° C.
Intrinsic viscosity of PE in tetralin at 140° C.: 0.53 dl/g
Catalyst activity: 12143 moles of ethene reacted per mole of nickel.

EXAMPLE 3

50 mMoles of bis(cyclooctadiene)nickel-(O) in approximately 200 ml of anhydrous, nitrogen-saturated toluene are mixed under an inert gas atmosphere (nitrogen or argon) with equivalent quantities of benzoyl methylene triphenyl phosphorane and methylene trimethyl phosphorane. The resulting mixture is then heated to from 40° to 60° C. with intensive stirring for about 2 hours. After Schlenk filtration, the dark yellow-brown solution is concentrated in vacuo to half its volume. A first fraction of yellow crystals is formed on cooling to from 0° to −20° C., being isolated by Schlenk filtration, washed with hexane and dried in vacuo. The filtrate is treated in the same way, the first 3 crystalline fractions alone giving the pure compound 3.1 according to the present invention in a yield of approximately 80%. Impure fractions may be purified by recrystallisation, for example from toluene/hexane.

M.P.: 117°–120° C. with decomposition.

$C_{30}H_{32}OP_2Ni$, molecular weight, calculated 529.2, observed 528 (by mass spectroscopy for the $^{58}$Ni-isotope)

|  | % C | % H | % P | % Ni |
|---|---|---|---|---|
| Calculated: | 68.08 | 6.09 | 11.70 | 11.09 |
| Observed: | 67.8 | 6.1 | 11.7 | 11.0 |

ESCA-binding energies relative to C(1s)=284.6 eV: Ni($2p_{3/2}$)=854.8 eV, O(1s)=530.9 eV, P(2p)=132.0 eV.

Multinuclear NMR-data:
$^{31}$P H NMR in $C_6D_6/H_3PO_4$ ext
+17.4 ppm (d), +20.8 ppm (d), $^3J(^{31}P^{31}P)$=8 Hz.
$^{13}$C H NMR in $CD_2Cl_2$/TMS int
+7.3 ppm (dd, P$\underline{C}$H$_2$), $^1J(^{31}P^{13}C)$=65 Hz, $^2J(^{31}P^{13}C)$=30 Hz;
+15.4 ppm (d, H$_3\underline{C}$P), $^1J(^{31}P^{13}C)$=55 Hz;
+78.9 ppm (d, P$\underline{C}$H), $^1J(^{31}P^{13}C)$=52 Hz;
phenyl-carbon resonances 120 ppm to 156 ppm
+120.3 ppm (s); +125.2 ppm (s); +127.2 ppm (s);
+128.0 ppm (d, 3 Hz); +128.1 ppm (s); +128.6 ppm (s);
+128.9 ppm (s); +132.8 ppm (d, 10 Hz);
+135.9 ppm (d, 42 Hz); +138.8 ppm (d, 4 Hz);
+139.9 ppm (d, 13 Hz); +156.1 ppm (d, 31 Hz)
+182.1 ppm (d, PC$\underline{H}$CO,)$^2J(^{31}P^{13}C)$=25 Hz.
$^1$H NMR in $CD_2Cl_2$/TMS int
+0.65 ppm (dd, 2H), $^2J(^{31}P^1H)$=13 Hz, $^3J(^{31}P^1H)$=5 Hz;
+1.56 ppm (d, 9H), $^2J(^{31}P^1H)$=13 Hz;
+4.93 ppm (s, 1H)
+6.5 to 7.8 ppm (m, 20H).

Further examples of synthesised nickel catalysts are given in the following Table together with characteristic $^{31}$P NMR-shifts and molecular ions as identified by massspectroscopy for the $^{58}$Ni-isotope. As the first component for Examples 3.2 to 3.7 acetylmethylene triphenyl phosphorane and for Examples 3.8 to 3.10 benzoylmethylene triphenyl phosphorane and as the second component the given compounds are reacted.

|  |  | δ $^{31}P$ (ppm) | δ $^{31}P$ (ppm) | Mol ion |
|---|---|---|---|---|
| 3.2 | methylene triphenyl phosphorane | +18.5 | +34.1 |  |
| 3.2 | methylene triisopropyl phosphorane | +17.7 | +54.3 | 550 |
| 3.4 | methylene triethyl phosphorane | +17.8 | +41.1 |  |
| 3.5 | methylene trimethyl phosphorane | +17.8 | +21.7 | 466 |
| 3.6 | trimethylsilylmethylene triethyl phosphorane | +18.2 | +37.5 | 580 |
| 3.7 | phenylmethylene triisopropyl phosphorane | +22.6 | +43.0 |  |
| 3.8 | methylene trimethyl phosphorane | +17.4 | +20.8 | 528 |
| 3.9 | trimethylsilylmethylene triethyl phosphorane | +17.5 | +38.1 | 642 |
| 3.10 | phenylmethylene triiso- | +21.5 | +43.0 |  |

| | $\delta\ 31p$ (ppm) | $\delta\ 31p$ (ppm) | Mol ion |
|---|---|---|---|
| propyl phosphorane | | | 5 |

EXAMPLE 4

The polymerisation of ethene is performed as in Example 2, whereby pure compounds (marked by formula III) or "in-situ catalysts" (marked for formulae I and II) are applied.

(a) Catalyst 2 mMoles III ($R^1$, $R^2$, $R^3$, $R^4$, $R^5$, $R^6$=phenyl, $R^7$=methyl, $R^8$=H, X=$CH_2$) in 250 ml of toluene (multipulse injection)
Solvent: 4 liters of cyclohexane
Polymerisation pressure: 10 bars ethene
Polymerisation temperature: 80° C.
Total yield: 782 g (19% of oligomers)
PE melting point: 109° C.
Intrinsic viscosity of PE in tetralin at 120° C.: 0.06 dl/g
Catalyst activity: 13964 moles of ethene reacted per mole of nickel.

(b) Catalyst 2 mMoles I ($R^4$, $R^5$, $R^6$=phenyl, $R^7$=methyl, $R^8$=H), 4 mMoles II ($R^1$, $R^2$, $R^3$=isopropyl, X=$CH_2$) in 50 ml of toluene (single pulse injection)
Solvent: 1 liter of toluene
Polymerisation pressure: 90 bars ethene
Polymerisation temperature: 110° C.
Total yield: 586 g (18% of oligomers)
PE melting point: 111° C.
Intrinsic viscosity of PE in tetralin at 120° C.: 0.07 dl/g
Catalyst activity: 10464 moles of ethene reacted per mole of nickel.

(c) Catalyst 1 mMoles III ($R^1$, $R^2$, $R^3$=isopropyl, $R^4$, $R^5$, $R^6$=phenyl, $R^7$=methyl, $R^8$=H, X=$CH_2$) in 250 ml of toluene (multipulse injection)
Solvent: 1 liter of methylenechloride
Polymerisation pressure: 10 bars ethene
Polymerisation temperature: 95° C.
Total yield: 536 g (11% of oligomers )
PE melting point: 105° C.
Intrinsic viscosity of PE in tetralin at 120° C.: 0.07 dl/g
Catalyst activity: 19143 moles of ethene reacted per mole of nickel.

(d) Catalyst 2 mMoles III ($R^1$, $R^2$, $R^3$=ethyl, $R^4$, $R^5$, $R^6$=phenyl, $R^7$=methyl, $R^8$=H, X=$CH_2$) in 250 ml of toluene (miltipulse injection)
Solvent: 1 liter of cyclohexane
Polymerisatin pressure: 100 bars ethene
Polymerisation temperature: 115° C.
Total yield: 993 g (2% of oligomers)
PE melting point: 110° C.
Intrinsic viscosity of PE in tetralin at 120° C.: 0.06 dl/g
Catalyst activity: 17732 moles of ethene reacted per mole of nickel. (e) Catalyst 2 mMoles III ($R^1$, $R^2$, $R^3$=isopropyl, $R^4$, $R^5$, $R^6$=phenyl, $R^7$=methyl, $R^8$=H,. $R^{10}$=phenyl, X=$CHR^{10}$) in 250 ml of toluene (multipulse injection)
Solvent: 4 liters of cyclohexane
Polymerisation pressure: 10 bars ethene
Polymerisation temperature: 80° C.
Total yield: 1775 g (4% of oligomers)
PE melting point: 116° C.
Intrinsic viscosity of PE in tetralin at 120° C.: 0.09 dl/g
Catalyst activity: 31696 moles of ethene reacted per mole of nickel.

(f) Catalyst 2 mMoles III ($R^1$, $R^2$, $R^3$=isopropyl, $R^4$, $R^5$, $R^6$, $R^{10}$=phenyl, $R^7$=methyl, $R^8$=H, X=$CHR^{10}$) in 250 ml of toluene (multipulse injection)
Solvent: 4 liters of toluene
Polymerisation pressure: 10 bars ethene
Polymerisation temperature: 80° C.
Total yield: 1366 g (5% of oligomers)
PE melting point: 116° C.
Intrinsic viscosity of PE in tetralin at 120° C.: 0.11 dl/g
Catalyst activity: 24393 moles of ethene reacted per mole of nickel (g) Catalyst 2 mMoles III ($R^1$, $R^2$, $R^3$=methyl, $R^4$, $R^5$, $R^6$, $R^7$=phenyl, $R^8$=H, X=$CH_2$) in 250 ml of toluene (multipulse injection)
Solvent: 32 liters of cyclohexane
Polymerisation pressure: 10 bars ethene
Polymerisation temperature: 90° C.
Total yield: 1174 g (11% of oligomers)
PE melting point: 118° C.
Intrinsic viscosity of PE in tetralin at 120° C.: 0.11 dl/g
Catalyst activity: 20964 moles of ethene reacted per mole of nickel.

(h) Catalyst 2 mMoles III ($R^1$, $R^2$, $R^3$=ethyl, $R^4$, $R^5$, $R^6$, $R^7$=phenyl, $R^8$=H, X=$CHR^{10}$, $R^{10}$=trimethyl silyl) in 250 ml of toluene (multipulse injection)
Solvent: 4 liters of cyclohexane
Polymerisation pressure: 10 bars ethene
Polymerisation temperature: 105° C.
Total yield: 712 g (13% of oligomers)
PE melting point: 116° C.
Intrinsic viscosity of PE in tetralin at 120° C.: 0.08 dl/g
Catalyst activity: 12714 moles of ethene reacted per mole of nickel.

(i) Catalyst 2 mMoles III ($R^1$, $R^2$, $R^3$=isopropyl, $R^4$, $R^5$, $R^6$, $R^7$, $R^{10}$=phenyl, $R^8$=H, X=$CHR^{10}$) in 250 ml of toluene (multipulse injection)
Solvent: 1 liter of cyclohexane
Polymerisation pressure: 100 bars ethene
Polymerisation temperature: 90° C.
Total yield: 1388 g (0% of oligomers)
PE melting point: 118° C.
Intrinsic viscosity of PE in tetralin at 120° C.: 0.10 dl/g
Catalyst activity: 24785 moles of ethene reacted per mole of nickel.

(j) Catalyst 1 mMoles I ($R^4$, $R^5$, $R^6$, $R^7$=phenyl, $R^8$=$SO_3Na$), 1 mMoles II ($R^1$, $R^2$, $R^3$=phenyl, $R^{10}$=CH=CH—phenyl, X=$CHR^{10}$) with only 1 mMole of bis-(cyclooctadiene)-Nickel in 50 ml of toluene (singlepulse injection)
Solvent: 1 liter of cyclohexane
Polymerisation pressure: 100 to 200 bars ethene
Polymerisation temperature: 110° C.
Total yield: 333 g (0% of oligomers)
PE melting point: 129° C.
Intrinsic viscosity of PE in tetralin at 140° C.: 1.55 dl/g
Catalyst activity: 11893 moles of ethene reacted per mole of nickel.

We claim:

1. Nickel compounds producible by reacting a nickel-(O)-compound or a nickel compound convertible thereto in situ with two different compounds corresponding to the following general formulae $$\begin{array}{c} R^6 \quad R^8 \\ \diagdown \quad | \\ R^5-P=C-C=O \\ \diagup \quad | \\ R^4 \quad (I) \quad R^7 \end{array} \quad \text{and} \quad \begin{array}{c} R^3 \\ \diagdown \\ R^2-P=X \\ \diagup \\ R^1 \quad (II) \end{array}$$

wherein $R^1$, $R^2$ and $R^3$, which may be the same or different, represent optionally by halogen, hydroxy, $C_1-C_{20}$-alkoxy or $C_6-C_{12}$-aryloxy substituted $C_1-C_{20}$-alkyl radicals, $C_6-C_{12}$-aryl radicals or $C_3-C_8$-cycloalkyl radicals; $C_6-C_{12}$-aryl-$C_1-C_{20}$-alkyl radicals, $C_1-C_{20}$-alkyl-$C_6-C_{12}$-aryl radicals, $C_1-C_{20}$-alkyl-$C_3-C_8$-cycloalkyl radicals, $C_6-C_{12}$-aryl-$C_3-C_8$-cycloalkyl radicals $C_2-C_6$-alkenyl radicals, $C_6-C_{12}$-aryl-$C_2-C_6$-alkenyl radicals, di-$C_1-C_4$-alkylamino radicals and optionally substituted phenoxy and alkoxy radicals X denotes O, $NR^9$ or $$C \diagup^{R^{10}}_{\diagdown R^{11}}$$

$R^4$, $R^5$, $R^6$, $R^7$ and $R^8$, which may be the same or different, represent optionally by halogen, hydroxy, $C_1-C_{20}$-alkoxy or $C_6-C_{12}$-aryloxy substituted $C_1-C_{20}$-alkyl radicals, $C_6-C_{12}$-aryl radicals, $C_2-C_{30}$-alkenyl radicals or $C_3-C_8$-cycloalkyl radicals; $C_6-C_{12}$-aryl-$C_1-C_{20}$-alkyl radicals, $C_1-C_{20}$-alkyl-$C_6-C_{12}$-aryl radicals halogen, hydroxy, $C_1-C_{20}$-alkoxy radicals, or $C_6-C_{12}$-aryloxy radicals, in addition to which $R^7$ may represent hydrogen, $R^8$ may represent hydrogen or sulphonate and $R^9$, $R^{10}$ and $R^{11}$, which may be the same or different represent hydrogen, silyl, halogen, nitrophenyl, cyano or $R^1$.

2. Compounds as claimed in claim 1 wherein $R^1$, $R^2$ and $R^3$, which may be the same or different, represent $C_1-C_6$-alkyl, cyclohexyl, phenyl, tolyl, benzyl, di-$C_1-C_4$-alkylamino, phenoxy or $C_1-C_4$-alkoxy, $R^4$ represents $C_6-C_{12}$-aryl;

$R^5$, $R^6$, $R^7$ and $R^8$, which may be the same or different, represent $C_1-C_4$-alkyl, cyclohexyl, phenyl, tolyl, benzyl or vinyl; in addition to which $R^7$ may represent hydrogen or $C_1-C_4$-alkoxy and $R^8$ may represent hydrogen or sulphonate and $R^9$, $R^{10}$ and $R^{11}$ denotes hydrogen, chlorine, cyano, trimethyl silyl, $C_1-C_6$-alkyl, phenyl, chlorophenyl, nitrophenyl, $C_1-C_6$-alkylphenyl, $C_2-C_6$-alkenyl, and phenyl-$C_2-C_6$-alkenyl.

3. A process for producing the compounds claimed in claim 1, characterised in that a nickel-(O) compound or a compound convertible thereto in situ is reacted with a compound corresponding to the following general formula:

$$\begin{array}{c} R^6 \quad R^8 \\ \diagdown \quad | \\ R^5-P=C-C=O \\ \diagup \quad | \\ R^4 \quad R^7 \end{array} \quad (I)$$

and with compound corresponding to the following general formula:

$$\begin{array}{c} R^3 \\ \diagdown \\ R^2-P=X \\ \diagup \\ R^1 \end{array} \quad (II)$$

wherein the substituents $R^1$ to $R^8$ and X are as defined in claim 1.

4. A process as claimed in claim 3, characterised in that from 1 to 4 moles of the compound I and from 1 to 4 moles of the compound II are reacted per mole of the nickel-(O) compound.

5. A process as claimed in claim 3, characterised in that 1 mole of each of the compounds I and II is reacted per mole of the nickel-(O) compound.

6. A process as claimed in claim 3, characterised in that the reactants are reacted with one another at from 0° to 100° C. under anaerobic conditions.

* * * * *